United States Patent
Behiels

(10) Patent No.: US 7,796,792 B2
(45) Date of Patent: Sep. 14, 2010

(54) METHOD OF IDENTIFYING DISTURBING FREQUENCIES ORIGINATING FROM THE PRESENCE OF AN ANTI-SCATTER GRID DURING ACQUISITION OF A RADIATION IMAGE

(75) Inventor: Gert Behiels, Edegem (BE)

(73) Assignee: Agfa HealthCare, N.V., Mortsel (BE)

( * ) Notice: Subject to any disclaimer, the term of this patent is extended or adjusted under 35 U.S.C. 154(b) by 1089 days.

(21) Appl. No.: 11/471,793

(22) Filed: Jun. 21, 2006

(65) Prior Publication Data
US 2007/0003125 A1 Jan. 4, 2007

Related U.S. Application Data

(60) Provisional application No. 60/699,685, filed on Jul. 15, 2005.

(30) Foreign Application Priority Data
Jun. 29, 2005 (EP) .................. 05105782

(51) Int. Cl.
*G06K 9/00* (2006.01)
(52) U.S. Cl. .................. 382/128; 128/922
(58) Field of Classification Search ......... 382/128–132, 382/260, 261, 275; 128/922; 345/629; 378/86, 378/87, 163, 164
See application file for complete search history.

(56) References Cited

U.S. PATENT DOCUMENTS

| 5,661,818 | A | * | 8/1997 | Gaborski et al. | ............. 382/132 |
| 6,163,589 | A | * | 12/2000 | Vartanian | .................. 378/7 |
| 6,269,176 | B1 | * | 7/2001 | Barski et al. | ................ 382/128 |
| 6,333,990 | B1 | * | 12/2001 | Yazici et al. | ................ 382/132 |
| 6,470,072 | B1 | * | 10/2002 | Johnson | .................. 378/154 |
| 6,630,660 | B1 | * | 10/2003 | Finn | ................ 250/237 G |
| 6,995,387 | B2 | * | 2/2006 | Vuylsteke et al. | ........... 250/584 |
| 7,050,618 | B2 | * | 5/2006 | Belykh et al. | ............... 382/132 |
| 7,142,705 | B2 | * | 11/2006 | Inoue et al. | .................. 382/132 |
| 7,174,038 | B2 | * | 2/2007 | Belykh et al. | ............... 382/132 |
| 7,336,811 | B2 | * | 2/2008 | Takeo | ......................... 382/132 |
| 7,479,969 | B2 | * | 1/2009 | Behiels | ....................... 345/629 |
| 2005/0031182 | A1 | | 2/2005 | Inoue | |

FOREIGN PATENT DOCUMENTS

EP 1 505 540 A 2/2005

OTHER PUBLICATIONS

Belykh et al "Antiscatter stationary grid artifacts automated detection and removal in projection radiography images", Medical Imaging 2001: Image Processing, Milan Sonka, Kenneth M. Hanson, Editors, 1162 Proceedings of SPIE vol. 4322 (2001).*

D. R. Dance and G. J. Day. Computation of scatter in mammography by monte carlo methods. Physics in Medicine and Biology, 29:237 { 247, 1984.*

European Search Report EP 05 10 5782 (Nov. 25, 2005).

\* cited by examiner

*Primary Examiner*—Vu Le
*Assistant Examiner*—Andrae S Allison
(74) *Attorney, Agent, or Firm*—Leydig, Voit & Mayer, Ltd.

(57) ABSTRACT

A method of determining disturbing signal frequencies in a signal representation of radiation image originating from the presence of an anti-scatter grid during image acquisition, the signal representation being generated by an image read out and digitizing process, whereby the digitizing of an image of a simulated anti-scatter grid is simulated and the signal resulting from this simulation is evaluated to determine the disturbing frequencies.

7 Claims, 2 Drawing Sheets

METHOD OF IDENTIFYING DISTURBING FREQUENCIES ORIGINATING FROM THE PRESENCE OF AN ANTI-SCATTER GRID DURING ACQUISITION OF A RADIATION IMAGE

FIELD OF THE INVENTION

The present invention relates to method of identifying disturbing frequencies originating from the use of an anti scatter grid during radiation image recording in computed radiography.

BACKGROUND OF THE INVENTION

A commonly used technique to reduce the amount of scattered X-rays in computed radiography, digital radiography as well as classical film-based X-ray systems is the use of anti-scatter grids. These grids are lead foil strips, placed apart at a certain distance in a suitable covering.

There exist different types of anti-scatter grids. In parallel grids, the lead foil strips are parallel, while in honeycomb grids the strips are placed in a honeycomb pattern. The grids are stationary or moving. The use of these grids effectively reduces the radiation scattering but occasionally introduces artifacts such as grid lines into the image.

In a moving system, the motion of the grids removes the grid lines in the image. However, in some circumstances e.g. short exposure time or malfunctioning of the system, the artifacts remain in the image. With stationary grids, the grid lines are almost always visible.

If the image is formed digitally or converted afterwards to a digital image representation, Moiré artifacts may appear when displaying the image at a certain scale. These low frequent Moiré artifacts are mostly disturbing and should be eliminated. Before displaying the image, the grid lines, if present in the image, should be removed.

Current gridline correction techniques, when having detected a grid, suppress only the fundamental frequency in the image sometimes in combination with frequencies in the neighborhood of the harmonic frequencies. The assumption of the harmonic frequencies is not always true. The number of harmonic frequencies to be suppressed is fixed in the prior art methods.

It is an object of the present invention to provide a method to determine the disturbing frequencies in a signal representation of a radiation image that overcomes the above-mentioned shortcoming of the prior art.

SUMMARY OF THE INVENTION

The above-mentioned aspects are realised by a method as set out in claim 1.

Specific features for preferred embodiments of the invention are set out in the dependent claims.

Further advantages and embodiments of the present invention will become apparent from the following description and drawings.

The present invention determines which frequencies to suppress in an image signal representing an image originating from an x ray exposure whereby an anti scatter grid has been used in order to remove the annoying Moiré artifacts.

Having found the fundamental frequency of the anti scatter grid in a signal representation of an x ray image, the digitization of an image containing only an anti scatter grid is simulated. Next, spectrum analysis, e.g. Fourier analysis of this simulated digitized signal is used to determine which frequencies the image might be disturbed by the presence of the anti scatter grid. If the candidate frequencies are also present in the image, they are selected as frequencies to suppress.

The dash-dotted line is the signal representation of a simulated grid, drawn at a higher resolution than the scanning resolution (pixel positions) of a read out device used for reading out a stored radiation image.

The dotted line shows the simulated signal after simulation of the digitization process of the digitizer. It is clear that the simulated signal contains more frequencies than only the fundamental frequency.

Figure 1:
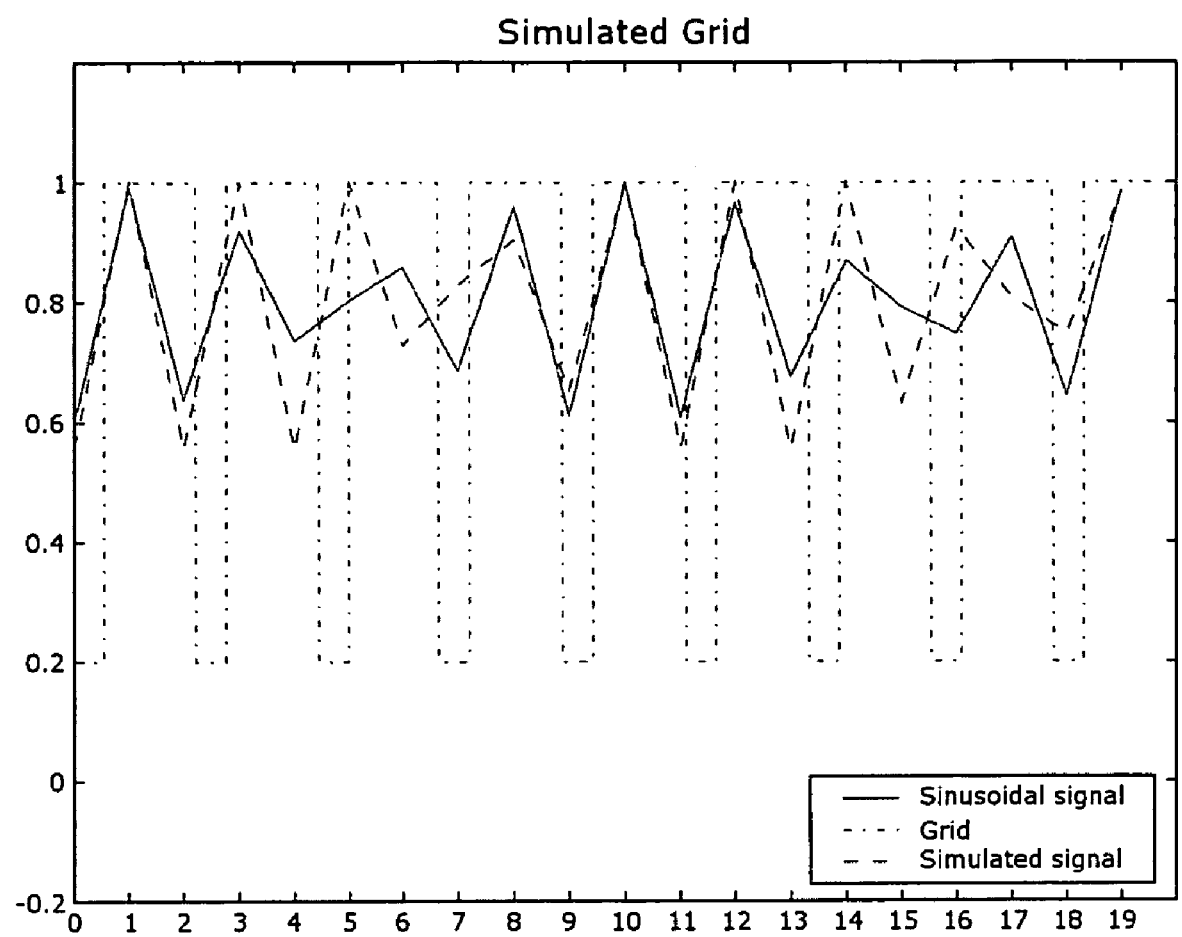
FIG. 1 shows the expected signal representation of a grid image at the pixel positions when only the fundamental frequency is taken into account (solid line).
Figure 2:
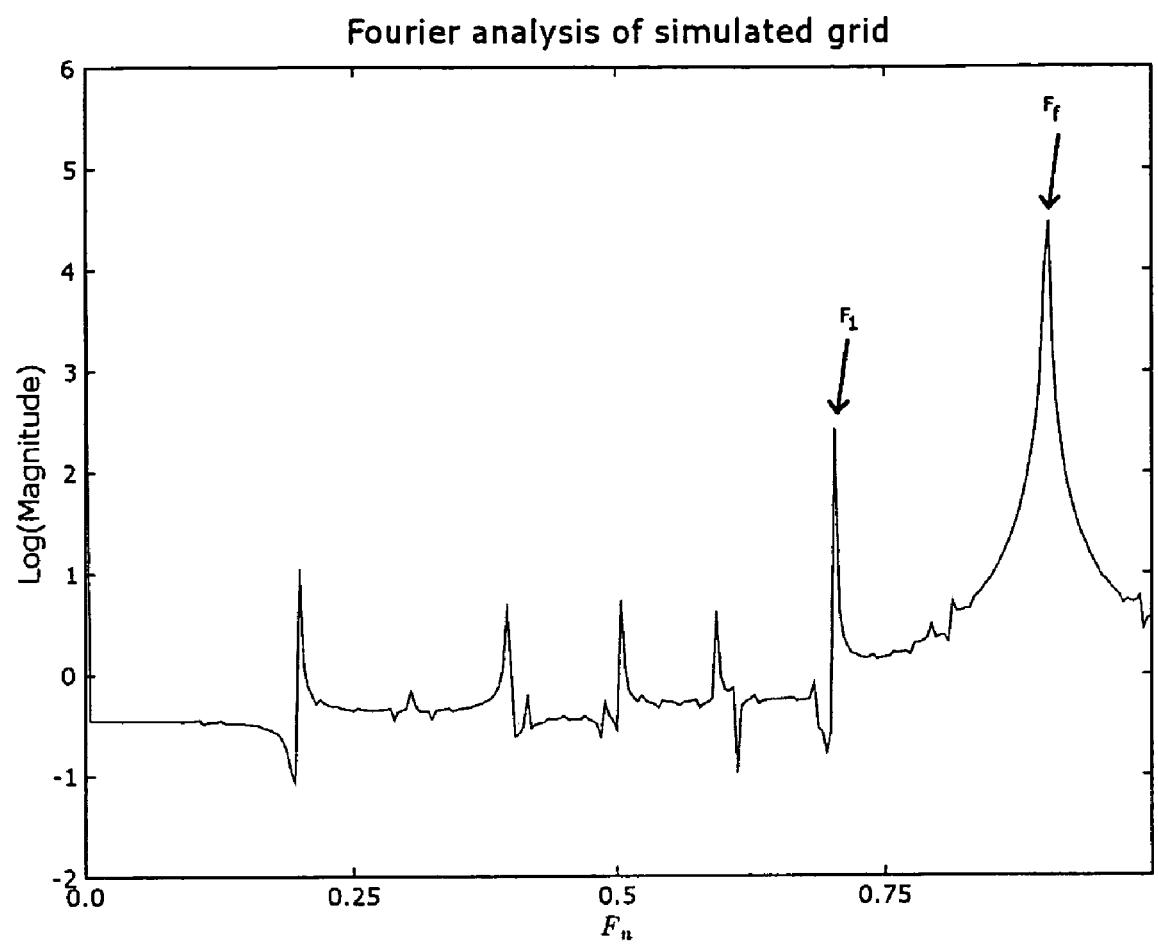

FIG. 2 shows the result of a Fourier analysis of the simulated grid signal. If we want to suppress the frequencies for which the log magnitude is greater than 2, the relative frequency $F_1$, at about 70% of the Nyquist frequency, is a candidate frequency for suppression. $F_f$ is the fundamental frequency found in the image of the grid.

DETAILED DESCRIPTION OF THE INVENTION

A specific embodiment of the method of the present invention will be described hereinafter.

The input of the method is the fundamental frequency or period of the anti-scatter grid in an x-ray image of the grid.

In the context of the present invention the x-ray image of the grid is obtained by means of a computed radiography system. The grid is irradiated by means of x-rays. The radiation image of the grid is stored in a radiation detector such as a photostimulable phosphor screen. The image is then read out in a read out device (also called digitizer) by scanning the screen with stimulating radiation. Image-wise modulated light emitted by the exposed screen upon stimulation is detected and converted into a signal representation.

The signal representation is analysed and the frequency at which the signal of the anti-scatter grid has maximum amplitude, hereinafter called the fundamental frequency $F_f$, with corresponding period $P_f$, is detected. This fundamental frequency does not necessarily coincide with the true grid frequency $F_g$, with corresponding period $P_g$.

If $F_s$ is the sampling frequency of the digitizer and $F_n$ the corresponding Nyquist frequency $$F_n = \frac{F_s}{2},$$

one could try to guess the true grid frequency $F_g$. Having found this true grid frequency, the corresponding $h^{th}$ harmonic frequency to suppress in the image signal is $$|F_h| = |k \cdot F_s - h \cdot F_g|, \quad \text{Equation 1}$$

where k is choosen to satisfy $$|F_h| \leq F_n.$$

The success of this scheme lies entirely in the exact guess of $F_g$ and the selection of enough harmonic frequencies to suppress in the image signal. Because we do not know how many frequencies to suppress, a different approach is preferably chosen.

Having detected the fundamental frequency $F_f$ in the signal representation of the radiation image of the grid, a grid is simulated.

For this purpose a signal representation is generated representing a grid with the distance between two grid lamella's being equal to $P_f$. This grid signal representation g is constructed at a higher resolution than the sampling frequency $F_s$ of the read out apparatus:

$$g_i = \begin{cases} a : 0 \leq i \bmod P_g < r \\ 1 : r \leq i \bmod P_g < P_g \end{cases}$$

$$\begin{cases} 0 \leq a < 1 \\ 0 \leq r < 1 \end{cases}$$

If the pixel size $P_s$ is for example 100 μm, the grid is constructed at a resolution where one sample i represents 1 μm, a is the attenuation of the radiation at the positions of the grid lamella's and r is the ratio of the lamella width to the distance between two lamella's.

This grid signal representation is then averaged over distance $P_s$ to obtain the simulated grid signal representation G:

$$G_j = \sum_{j=iP_s}^{(i+1)P_s - 1} g_j.$$

This averaging simulates the digitization process of the image read out device.

More complex simulations may be used, such as averaging the grid after convolution with a Gaussian kernel to simulate the flying spot of the light stimulation in some digitizers.

For most purposes, a simple averaging of the grid at the high resolution is sufficient.

Fourier analysis of the simulated grid representation G shows at which frequencies the original image signal is disturbed (see FIG. 2).

Only the frequencies $F_h$, with an amplitude greater than a fixed threshold, are selected.

In the example of FIG. 2, in addition to the fundamental frequency $F_f$ located at about 0.9 times the Nyquist frequency, we also want to suppress the frequency located at about 0.7 times the Nyquist frequency.

The frequencies to be suppressed can be stored in a look up table with the fundamental frequency as the indexing variable and retrieved when these frequencies are to be suppressed in order to eliminate the disturbing effect in an image due to the presence of an anti-scatter grid at image recording.

The entries of the look up table can thus be obtained by the steps described higher, alternatively they can be obtained by image analysis, e.g. by applying equation (1).

The invention claimed is:

1. A method of determining disturbing signal frequencies in a signal representation of radiation image originating from the presence of an anti-scatter grid during image acquisition, said signal representation being generated by an image read out and digitizing process, characterized by the steps of simulating the digitizing process of an image of a simulated anti-scatter grid thereby generating a digitized simulated anti-scatter grid signal, analyzing said digitized simulated anti-scatter grid signal to determine said disturbing frequencies.

2. A method according to claim 1 wherein said analyzing step comprises applying a Fourier transformation to said digitized, simulated anti-scatter grid signal.

3. A method according to claim 1 wherein a frequency of the simulated anti-scatter grid equals a fundamental frequency measured in said signal representation of said image representation of said anti-scatter grid in said radiation image.

4. A method according to claim 1 wherein a frequency of the simulated anti-scatter grid equals an actual frequency of said anti-scatter grid.

5. A method according to claim 1 wherein a frequency of the simulated anti-scatter grid equals an estimated grid frequency.

6. A method according to claim 1 wherein the disturbing frequencies resulting from said analyzing step which are prominently present in said signal representation of said radiation image are retained to be suppressed.

7. A method according to claim 1 wherein said disturbing frequencies are stored in a look up table.

* * * * *